(12) United States Patent
Ilisie et al.

(10) Patent No.: US 11,448,780 B2
(45) Date of Patent: Sep. 20, 2022

(54) DEVICE FOR THE DETECTION OF GAMMA RAYS WITH ACTIVE PARTITIONS

(71) Applicants: UNIVERSITAT POLITÈCNICA DE VALÉNCIA, Valencia (ES); CONSEJO SUPERIOR DE INVESTIGACIONES CIENTÍFICAS (CSIC), Madrid (ES)

(72) Inventors: Victor Ilisie, Valencia (ES); Jose Maria Benlloch Baviera, Valencia (ES); Filomeno Sanchez Martinez, Valencia (ES)

(73) Assignees: UNIVERSITAT POLITECNICA DE VALENCIA, Valencia (ES); CONSEJO SUPERIOR DE INVESTIGACIONES CIENTIFICAS (CSIC), Madrid (ES)

( * ) Notice: Subject to any disclaimer, the term of this patent is extended or adjusted under 35 U.S.C. 154(b) by 14 days.

(21) Appl. No.: 17/289,453

(22) PCT Filed: Oct. 30, 2019

(86) PCT No.: PCT/ES2019/070737
§ 371 (c)(1),
(2) Date: Apr. 28, 2021

(87) PCT Pub. No.: WO2020/089501
PCT Pub. Date: May 7, 2020

(65) Prior Publication Data
US 2022/0011451 A1 Jan. 13, 2022

(30) Foreign Application Priority Data
Oct. 31, 2018 (ES) ............... ES201831058

(51) Int. Cl.
*A61B 6/00* (2006.01)
*G01T 1/20* (2006.01)
(Continued)

(52) U.S. Cl.
CPC .......... *G01T 1/20184* (2020.05); *A61B 6/037* (2013.01); *A61B 6/06* (2013.01);
(Continued)

(58) Field of Classification Search
CPC . G01T 1/20184; G01T 1/1642; G01T 1/2002; G01T 1/2018; G01T 1/249;
(Continued)

(56) References Cited

U.S. PATENT DOCUMENTS

2003/0111609 A1* 6/2003 Zeng ............... G01T 1/1648
250/363.1
2006/0000978 A1 1/2006 Engdahl et al.
(Continued)

FOREIGN PATENT DOCUMENTS

| CN | 106405619 A | 2/2017 |
|----|-------------|--------|
| EP | 1598863 A1 | 11/2005 |
| WO | 2012005128 A1 | 1/2012 |

OTHER PUBLICATIONS

Greta S. P. Mok, "The effects of object activity distribution on multiplexing multi-pinhole SPECT", Article, 2011, 2635-2650, vol. 56, No. 8, Physics in Medicine and Biology.
(Continued)

*Primary Examiner* — Kiho Kim
(74) *Attorney, Agent, or Firm* — Hayes Soloway P.C.

(57) ABSTRACT

The invention relates to a device for the detection of gamma rays coming from a source without image truncation and without image overlapping, comprising, at least, two detection cells and each of said cells comprising a detection space adapted to receive the gamma rays that penetrate through an opening, wherein said detection space comprises one or more detection assemblies, with some of said assemblies being positioned such that they stand in the way of the gamma rays coming into the overlap volume thereof.

15 Claims, 5 Drawing Sheets

(51) Int. Cl.
*A61B 6/03* (2006.01)
*A61B 6/06* (2006.01)
*G01T 1/164* (2006.01)

(52) U.S. Cl.
CPC .......... *A61B 6/4258* (2013.01); *G01T 1/1642* (2013.01); *G01T 1/2002* (2013.01)

(58) Field of Classification Search
CPC ........... G01T 1/1644; G01T 1/20; G01T 1/22; A61B 6/037; A61B 6/06; A61B 6/4258; A61B 6/00; G21K 1/025; G21K 1/00
See application file for complete search history.

(56) References Cited

U.S. PATENT DOCUMENTS

| | | |
|---|---|---|
| 2006/0065840 A1 | 3/2006 | Joung et al. |
| 2012/0232385 A1 | 9/2012 | Hattori et al. |
| 2013/0158389 A1 | 6/2013 | O'Conner et al. |
| 2013/0267056 A1 | 10/2013 | Fushie et al. |
| 2014/0175296 A1 | 6/2014 | Benlloch Baviera et al. |

OTHER PUBLICATIONS

Lindsay C. Johnson, "Reducing Multiplexing Artifacts in Multi-Pinhole SPECT with a Stacked Silicon-Germanium System: a Simulation Study", Article, 2014, 2342-2351, vol. 33, No. 12, IEEE Transactions on Medical Imaging.

Greta S. P. Mok, "Quantification of the Multiplexing Effects in Multi-Pinhole Small Animal SPECT: A Simulation Study", Article, 2009, 2636-2643, vol. 56, No. 5, IEEE Transactions on Nuclear Science.

Oleksandra Ivashchenko, "Quarter-Millimeter-Resolution Molecular Mouse Imaging with U-SPECT", Article, 2014, 1-8, Molecular Imaging.

Kathleen Vunckx, "Effect of Overlapping Projections on Reconstruction Image Quality in Multipinhole SPECT", Article, 2008, 972-983, vol. 27, No. 7, IEEE Transactions on Medical Imaging.

* cited by examiner

FIG. 1 (state of the art)

FIG. 2 (state of the art)

FIG. 3a (state of the art)

FIG. 3b (state of the art)

DEVICE FOR THE DETECTION OF GAMMA RAYS WITH ACTIVE PARTITIONS

CROSS-REFERENCE TO RELATED APPLICATIONS AND PRIORITY

This patent application claims priority from PCT Patent Application No. PCT/ES2019/070737 filed Oct. 30, 2019, which claims priority from Spanish Patent Application No. P201831058 filed Oct. 31, 2018. Each of these patent applications are herein incorporated by reference in its/their entirety.

FIELD OF THE INVENTION

The present invention is comprised in the field relating to imaging by means of gamma rays. More specifically, the invention relates to the design of devices for the detection of gamma radiation to obtain information about same, for example nuclear imaging medical devices, such as gamma cameras or single photon emission computed tomography (SPECT) equipment, among others.

BACKGROUND OF THE INVENTION

High-sensitivity and high-resolution gamma cameras are of particular interest today, given that they present a high potential in the field of the nuclear medicine. Said cameras allow, for example, small-sized tumors to be diagnosed early, and are also useful in a wide range of pre-clinical studies, which allows, for example, more effective treatments against cancer to be designed. The basic operation of a gamma camera device consists of injecting into a patient a radioactive contrast agent, such as $^{99m}$Tc, which will break down, emitting a photon (gamma ray) of 140 keV of energy, according to the following process:

$$^{99m}Tc \rightarrow {}^{99}Tc + \gamma. \quad \text{(Eq. 1)}$$

Figure 1:
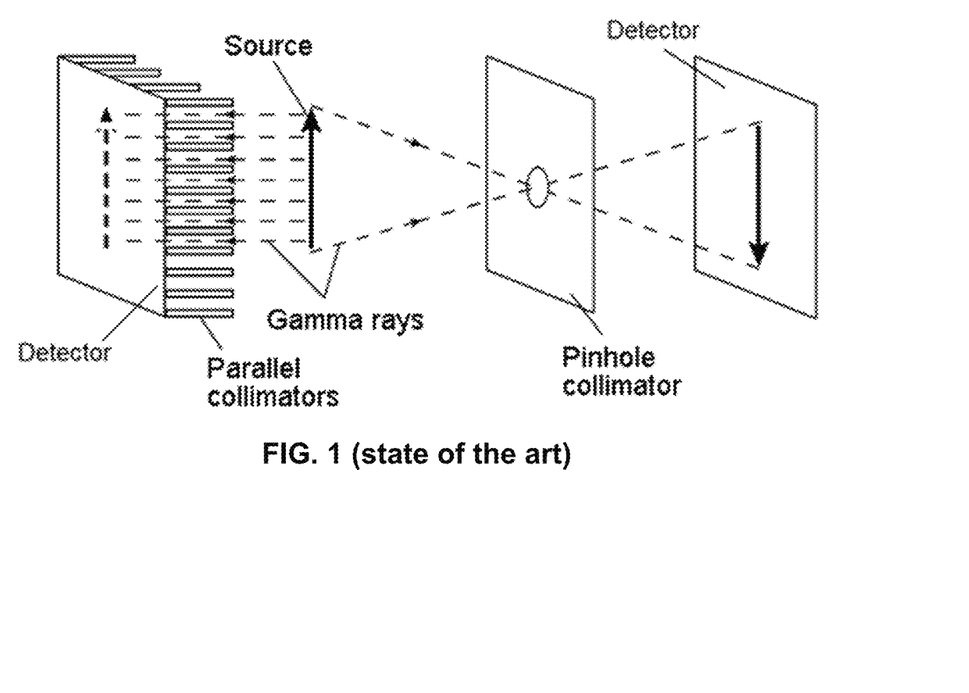
FIG. 1 schematically shows the operation of the two typical gamma camera devices of the state of the art, with parallel hole collimators (left) and with a pinhole collimator (right).

This high-energy photon passes through a collimator, preferably made of a dense material that is highly impenetrable for gamma rays in this energy range, typically formed by lead (Pb) or tungsten (W), before reaching a radiation sensitive detector. This process is shown schematically in FIG. 1 herein, for two typical types of collimators (with parallel holes on the left side of the image, and pinholes on the right side of the image).

Figure 2:
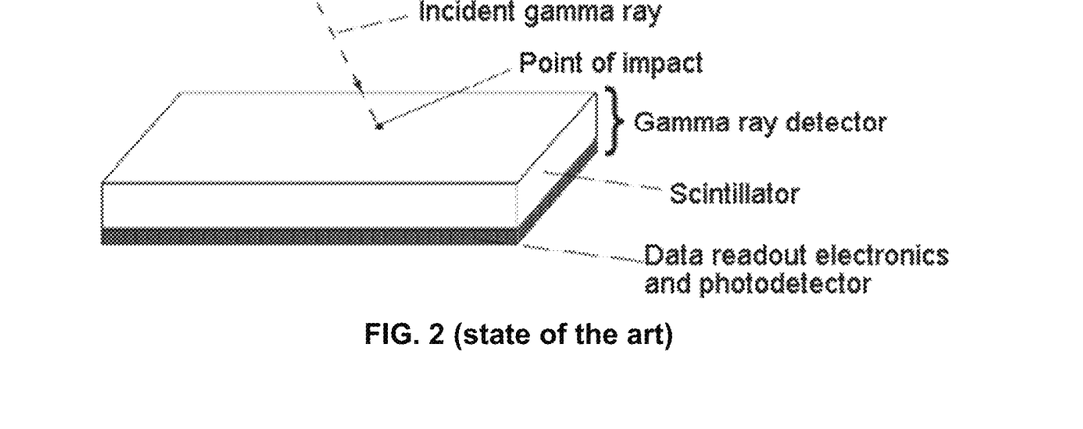
FIG. 2 shows a known gamma ray detector module, formed by a sensitive material such as a scintillation block (which produces optical photons as a consequence of the interaction of a gamma ray with the material), a photodetector (sensitive to optical photons) and readout electronics (in charge of processing the electronic signals of the photodetector).

Radiation-sensitive detectors of cameras of this type are usually made from a dense, gamma ray-sensitive material, typically a block of NaI scintillating crystal or the like. In said block, the gamma ray is absorbed by a nucleus or electron of the material, the energy of which is emitted again in the form of a quantity in the order of thousands of optical photons, which are detected by a photodetector. This process is shown schematically in FIG. 2 herein.

Figure 3A:
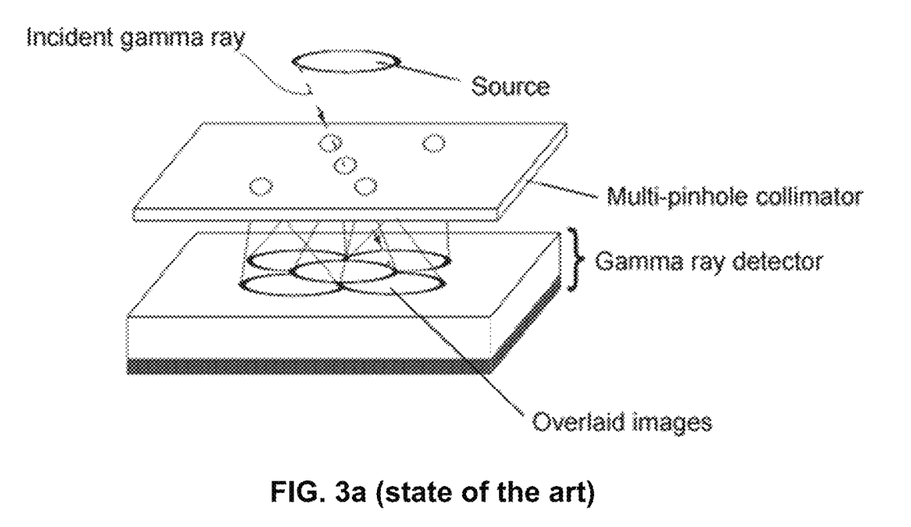
FIG. 3a shows the problem of multiplexing in a multi-pinhole collimator. The incident gamma rays of the source of radiation pass through the openings before reaching the detector. Depending on the geometry, the aperture and inclination of the openings, overlaid regions can be produced in the detector, which prevent unambiguously identifying the opening through which an impacting gamma ray has previously passed.
Figure 3B:
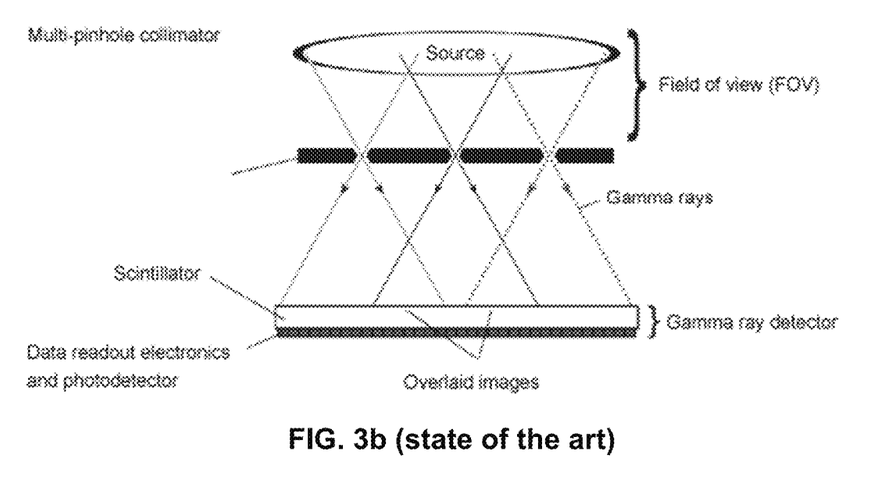

A common problem for gamma cameras is their low sensitivity. This is because only gamma rays which are emitted in parallel to the collimators (for the case of a parallel collimator, FIG. 1, left) or within a certain angular region (for the pinhole collimator, FIG. 1, right) effectively reach the detector. In this context, in the case of gamma cameras, with collimation openings, to increase sensitivity, which means increasing the number of gamma rays detected, the number of pinholes and/or the angular aperture of each pinhole must be increased. Nonetheless, by increasing the number of said openings, the unwanted effect known as image overlap (or the problem of multiplexing) is generated, as schematically shown in FIGS. 3a-3b, showing different perspectives of this effect. As is seen in said figures, within the overlap region of the detector it is impossible to unequivocally identify the opening through which the incident gamma ray has previously passed before it is detected. In the absence of this information, usually what is done is all the possible combinations are considered in the calculations performed in the image reconstruction method. As an example, in the case of positron emission tomography (PET), said reconstruction method consists of calculating lines of response (LOR) through the field of view (FOV). In the case of gamma cameras, LORs are constructed by merging the point of impact of the gamma ray in the detector with the corresponding opening (through which it previously passed). At this point, when the correct opening in the overlapping region cannot be identified and all the combinations of possible gamma ray paths have to be made, this translates into considering incorrect LORs for image reconstruction. This, therefore, introduces noise into the final reconstructed image, as well as possible spurious images, commonly referred to as artifacts (see, for example, in references [1], [2], [3] mentioned at the end of this section). In addition to being associated with images with noise, artifacts are highly dangerous given that they may have serious consequences in a possible incorrect diagnosis of patients (for clinical cases), or may lead to mistaken conclusions in pre-clinical studies.

The aforementioned problems also occur in known detectors based on collimators which do not produce overlapping, such as for example those described in patent applications US 2006/0065840 A1 and US 2006/0000978 A1. Nevertheless, in said detectors, the elimination of overlap causes, in contrast, the truncation of images and a smaller FOV (which may contain blind regions). In recent years, a number of studies have been performed to improve gamma cameras and SPECT systems (see mentioned references [1], [2], [3], [4]) to eliminate overlap effects. However, to date, no generic solution has been found which can be used in any detection system, given that the problem largely depends on the complexity of the object of study (small animals, organs, etc.), on the FOV or on the desired resolution, as well as on other design parameters. A practical solution that offers high sensitivity and resolution has been proposed in the SPECT/gamma camera described in reference [5], wherein the collimator has a large quantity of holes and is cylindrical. However, this system has the enormous drawback of its design involving a very small FOV. Therefore, its approach may only be applied effectively for pre-clinical studies with small animals. Also, as a consequence of the small FOV, when a large region of the body of the animal is to be studied, said body has to be moving during the scan, which greatly hinders the complete image taking process.

In view of the limitations of the state of the art described above, the present invention proposes a novel device for the detection of gamma rays, based on a new concept of active partitions which prevent not only the occurrence of overlap during imaging, but which furthermore has a full FOV and is applicable to various techniques in a completely general manner.

REFERENCES OF THE STATE OF THE ART MENTIONED

[1] G. S. P. Mok, B. M. W. Tsui y F. J. Beekman, "*The effects of object activity distribution on multiplexing multi-pinhole SPECT*", Phys. Med. Biol. 56 (2011) 2635-2650.

[2] L. C. Johnson, S. Shokouhi and T. E. Peterson, "*Reducing Multiplexing Artifacts in Multi-Pinhole SPECT with a*

*Stacked Silicon-Germanium System: a Simulation Study*", IEEE Trans. Med. Imaging (2014) 33(12): 2342-2351.

[3] G. S. P. Mok, Y. Wang, and B. M. W. Tsui, "*Quantification of the Multiplexing Effects in Multi-Pinhole Small Animal SPECT: A Simulation Study*", IEEE Trans. Nucl. Sci. 2009, 56(5): 2636-2643.

[4] K. Vunckx, P. Suetens, J. Nuyts, "*Effect of Overlapping Projections on Reconstruction Image Quality in Multipinhole SPECT*", IEEE Transactions on Medical Imaging, Vol. 27, No. 7 (2008).

[5] Ivashchenko O., van der Have F., Villena J. L., Groen H. C., Ramakers R. M., Weinans H. H., Beekman F. J., "*Quarter-Millimeter-Resolution Molecular Mouse Imaging with U-SPECT+*", Mol. Imaging (2014), 13. doi: 10.2310/7290.2014.00053.

BRIEF DESCRIPTION OF THE INVENTION

In light of the problems of the state of the art set forth in the preceding section, the device proposed by the present invention eliminates the problem of overlap/multiplexing, without producing the undesired effect of truncation and without generating artifacts in the obtained images, furthermore maintaining the property of high sensitivity in a multi-pinhole collimator, which translates into a high-resolution image for an arbitrarily large FOV.

The invention thereby maintains all the advantages of the multi-pinhole collimators, but furthermore adds a new gamma radiation-sensitive element, which is a detector element (radiation-sensitive material) acting as a collimator/partition and preventing gamma rays from reaching the overlaid regions. Said collimator will denoted as "active partition", because in addition to preventing overlapping regions, it also acts as a detector and, therefore, can measure the incident photon impact coordinates. All the information needed for image reconstruction with a high resolution in the FOV is thereby retrieved. Therefore, in the device of the invention there is only a virtual overlap, which allows the opening through which any gamma ray passes before being detected to be unambiguously identified. In the device, furthermore, active partitions are preferably provided with their own photodetectors and corresponding readout electronics.

In another preferred embodiment of the invention, a possible variation of this configuration is considered, wherein the side walls of the collimator do not comprise photodetectors or readout electronics, and wherein the detectors are located only at the base region (like in other multi-pinhole collimators). Nevertheless, in order to obtain the impact coordinates without losing information, collimators are equipped with optical reflective surfaces on the side walls for the purpose of preventing the loss of optical photons and for guiding them to the sensitive regions of the detector.

The preceding configurations are possible provided that the scintillator of the active partition is dense and/or thick enough to stop most of the incident gamma rays before they reach the contiguous active partition. To achieve this, using a thin W or Pb plate which is arranged between said active partitions is a possible option.

For the two mentioned main configurations of the device, the cones of incidence of the gamma rays represent the allowed regions wherein said gamma rays can penetrate due to the opening of the pinhole of the device. Detection cells formed by the areas housing each cone of incidence can be repeated as many times needed in order to obtain the desired characteristics of the gamma camera device, for example a certain FOV size being obtained. The angles of inclination and the openings of the pinholes may vary among cells in order to obtain the desired resolution of the device.

Additionally, the external outer faces of the entire device are preferably protected by an active or passive gamma radiation absorbing material in order to prevent background noise coming from areas outside the field of view of interest.

More specifically, the object of the invention is a device and a system for obtaining images comprising said device according to any of the claims proposed in the present patent application.

To better understand the invention, a set of definitions of some of the expressions used herein is provided below:

Interaction cloud: accumulation of any type of interactions of particles (photoelectric, Compton, Bremsstrahlung, Cherenkov, etc.) having at least one measurable magnitude, such as deposited energy, instantaneous time, electrical charge, etc. This "interaction cloud" is formed by one or more interactions that are spatially and/or temporally close enough to be experimentally indistinguishable.

Spatial information: any type of data that is a function of $N(N\leq 3)$ spatial dimensions, whether discrete or continuous, for example, energy deposited at a point with 3D coordinates (x,y,z).

Sensitive material: any physical material interacting with radiation, producing at least one measurable physical magnitude.

Detector: any device with the capacity to record a certain physical magnitude (such as for example spatial and/or temporal information and/or any other physical magnitude) corresponding to one or more interaction clouds. Spatial information can be obtained, for example, by means of processing the distribution of energy deposition and/or the distribution of the timestamp and/or the distribution of the electrical charge, etc. A detector can be made up of one or more sensitive materials, one or more acquisition devices (which will be defined below), and readout electronics which extract signals from said detector. For example, in a scintillation detector, by means of using a scintillating crystal the distribution of scintillation photons as well as the timestamp can be recorded by the detector. This provides spatial and temporal information, as well as information about the total energy deposited and the manner in which they have been distributed. Another example can be a Cherenkov detector, wherein the area, time and energetic information can be obtained from the Cherenkov radiation and its distribution. Detectors can have any possible shape and size. Furthermore, the readout of the detector can be extracted from one or more regions thereof. In general, the readout can be done from one or more planar surfaces (faces) of the detector. For example, in a rectangular shaped scintillation detector, signals can be extracted from one or more, up to six, of its faces. It would also be possible to use scintillation crystals or other curved, non-rectangular sensitive materials, in which case the readout would be adapted appropriately.

The terms "light reflective surface" and "optical reflective surface" will be used as synonyms and interpreted as any surface on which a substantial portion of the photons impacting it are reflected.

The terms "detector" and "radiation-sensitive detector" will be used interchangeably herein.

The expression "timestamp" refers to the time information recorded in any part of an acquisition device, corresponding to a detection event.

Active partition: this is an independent detector or a module made up of radiation-sensitive material, which is coupled to another detector (with the possibility of extracting the coordinates and/or the energy information and/or timestamp of an event) and can have some of its surfaces covered with Pb or W or any other material arranged to prevent an incident gamma ray from reaching an overlaid region of a multi-opening gamma camera. Some faces also can be surfaces which reflect light in order to prevent the loss of scintillated optical photons.

Event: this is defined as the total number of interactions that a single incident gamma ray and its secondary particles cause, until the initial energy thereof is completely or substantially lost (deposited, absorbed, etc.).

Acquisition device: this refers to a device used to extract one or more magnitudes processed by a detector, said device comprising one or more sensitive materials. For example, for a scintillation detector, the acquisition device can be made up of a photodetector made of photosensors which extract information about the scintillation photons produced in a crystal.

Gamma camera module: this refers to an assembly of detectors and/or active partitions, which may or may not be independent, may or may not have an identical structure, together with a pinhole collimator, which work together to create a single detector which can be used as a gamma camera device having a single pinhole.

Gamma camera device: this refers to an assembly of gamma camera modules which may or may not be independent, may or may not have an identical structure, which work together to create a single gamma camera detector with a higher sensitivity and/or resolution and/or larger FOV than a gamma camera of an independent module. The multi-pinhole collimator can be continuous (made of a single piece of material, not from attached modules), thus making the device simpler.

Detection system: this refers to an assembly of gamma camera modules and/or an assembly of gamma camera devices which may or may not be independent, may or may not have an identical structure, which may or may not work together, and that as a whole gather useful information for reconstructing the image of the analyzed object/subject/patient.

DESCRIPTION OF THE DRAWINGS

The preceding and other features and advantages will be better understood from the detailed description of the invention, as well as from the preferred embodiments referring to the attached drawings, in which:

FIG. 3b shows a two-dimensional cross section of the overlap problem shown in FIG. 3a.

FIG. 6 describes in two dimensions a variation of the device with active partitions of the invention. In this case, the active partitions only have photodetectors and readout and electronics connected directly in the upper part of one of the sides, where said detector may be absent or replaced with a reflective surface. They are furthermore coupled to a horizontal main detector. For each active partition, all its faces (except the one coupled to the main detector and the one coupled to the lateral detector) must comprise reflective elements to prevent the optical photons from being able to escape from the detection cell. By analyzing the impact pattern of said optical photons, it is possible to distinguish whether the interaction has taken place in the main detector or in the active partition, without losing impact information with respect to any of the photons in the cone of incidence.

REFERENCES NUMBERS USED IN THE DRAWINGS

| (1) | Gamma ray |
|---|---|
| (2) | Source of radiation |
| (3) | Detection cell |
| (4) | Collimation element |
| (5) | Opening |
| (6) | Cone of incidence of the gamma rays |
| (7) | Detection space |
| (8) | Assembly for the detection of gamma rays |
| (8') | Assembly for the detection (active partition) of gamma rays |
| (9) | Gamma radiation-sensitive material |
| (10) | Photodetectors |
| (11) | Overlap volume |
| (12) | Blocking surface |
| (13) | Reflective element |
| (14) | Covering or casing |

DETAILED DESCRIPTION OF THE INVENTION

A detailed description of the invention in reference to different preferred embodiments thereof is described below based on FIGS. 4-10 herein. Said description is provided for the purposes of illustrating but not limiting the claimed invention.

As described in the preceding sections, the present invention relates to a device with a high-sensitivity and high-resolution multi-pinhole collimator for the detection of gamma rays, with an arbitrarily large FOV, characterized by the fact that it eliminates overlap, without losing information. By means of using active partitions, the detector of the device is capable of obtaining the gamma ray impact coordinates and unequivocally assigning the opening through which said gamma ray has previously passed. With this information, a correct LOR can be constructed for each event and, therefore, all the problems associated with the occurrence of artifacts associated with the overlap and the image truncation associated with the non-overlap are avoided. The gamma ray impact coordinates in the detector of the device can be obtained by means of standard methods such as, for example, by means of the distribution of the number of optical photons produced by a scintillation crystal, the distribution of the electrical charge produced in a semiconductor detector, Cherenkov radiation detection, etc. The depth of interaction (DOI) in the detector of the device can also be obtained with standard methods.

Preferably and as shown in FIGS. 4-10, the device of the invention allows gamma rays (1) coming from a source (2) of radiation to be detected, wherein said device comprises at least two contiguous detection cells (3), and wherein each of said detection cells (3) comprises:

a collimation element (4) comprising an opening (5) through which the gamma rays (1) coming from the source (2) can penetrate, defining a cone (6) of incidence;

a detection space (7) adapted to receive the gamma rays (1) that penetrate through the opening (5), wherein said detection space (7) comprises one or more detection assemblies (8, 8'), equipped with at least one gamma radiation-sensitive material (9) and at least one photodetector (10) connected to electronic signal readout and processing means of said photodetector (10).

Figure 4:
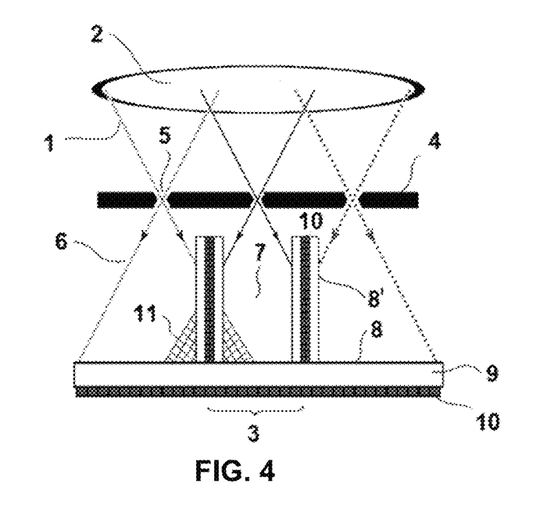
FIG. 4 describes in two dimensions the concept of "active partition" of the invention. In said figure, it can be observed how said active partition comprises an additional detector element, which is advantageously placed in the detection space, to prevent the gamma rays from reaching the overlapping area of the contiguous cell. Since said element, in addition to blocking rays, is also a detector, all the necessary information (coordinates of the impact and corresponding opening) can be retrieved as a result of the use of photodetectors and corresponding signal readout electronics.
Figure 8:
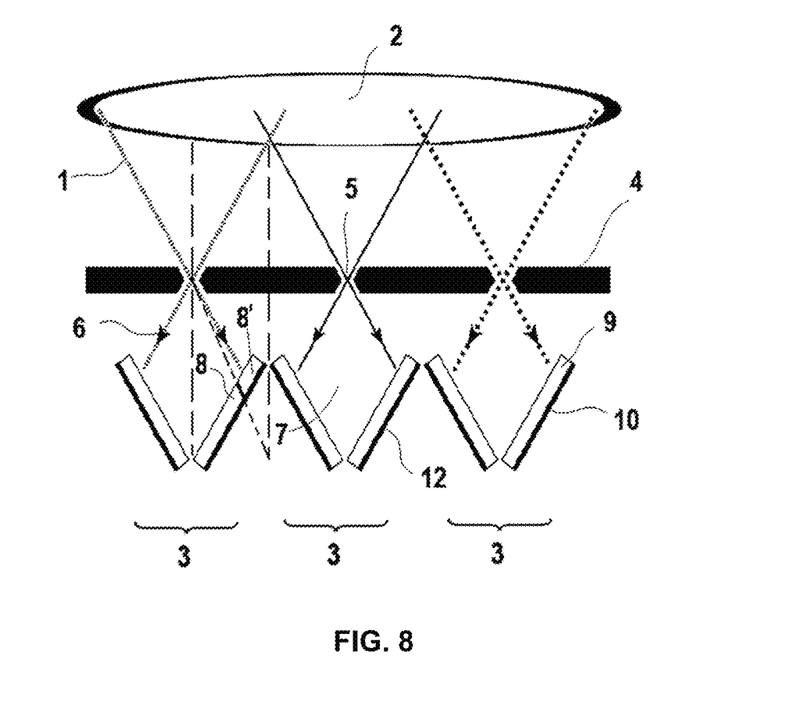
FIG. 8 describes in two dimensions another possible configuration of the active partitions in the device of the invention. In this case, the active partitions are inclined, and the horizontal main detector is not necessary. The retrieved information and the operation of the device are equivalent to those of the preceding configurations.

As seen in FIGS. 4 and 8 herein, the theoretical projections of the cones (6) of incidence of the gamma rays (1) in the two cells (3) have an overlap volume (11) within the detection space (7). Nevertheless, to prevent said overlap of the gamma rays (1) from effectively occurring in said volume (11), the detection assemblies (8') of the device of the invention are advantageously arranged within the detection space (7), such that they stand in the way of the paths of the gamma rays (1) the projection of which comes into the overlap volume (11) within said detection space. The device could furthermore optionally contain an additional blocking surface (12), made of Pb, W or the like, which prevents the passage of gamma rays (1) into the overlap volume (11). Any overlapping path of the gamma rays (1) is thereby blocked, but at the same time the device is capable of measuring the contribution of all of such rays in the absence of image truncation.

Figure 5:
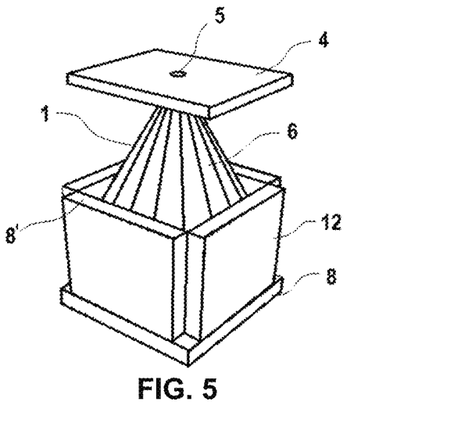
FIG. 5 shows a perspective view of a possible embodiment of the device of the invention equipped with four active partitions, a horizontal detector and a pinhole collimator. The main detector furthermore comprises a photodetector equipment and attached electronics. The active partitions may or may not have photodetectors and readout electronics. The cone of incidence schematically shows the area wherein the incident gamma rays can penetrate, due to the geometry and configuration of the pinhole collimator.
Figure 6:
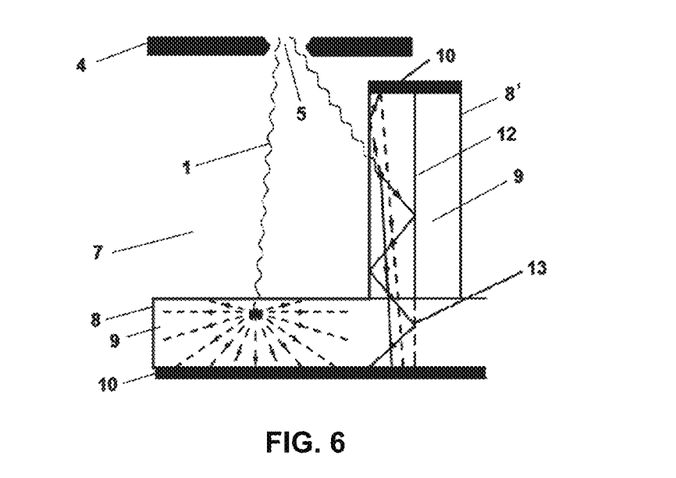

In a preferred embodiment of the invention shown in FIGS. 4 and 5, the photodetectors are arranged on the separating surface of the detection cells (3) which are in contact with the detection assemblies (8) of adjacent cells (3).

Preferably, the walls of the detection cells (3) and/or the detection assemblies (8, 8') comprise one or more reflective elements (13) for guiding the paths of the gamma rays (1). This embodiment is shown schematically in FIG. 6, wherein it can be seen how said reflective elements (13) allow the paths to be guided to the photodetectors (10) of the device, thus complying with the dual function thereof of eliminating any overlapping scenario of the gamma rays (1), but without causing any truncation of the obtained images.

Figure 7A:
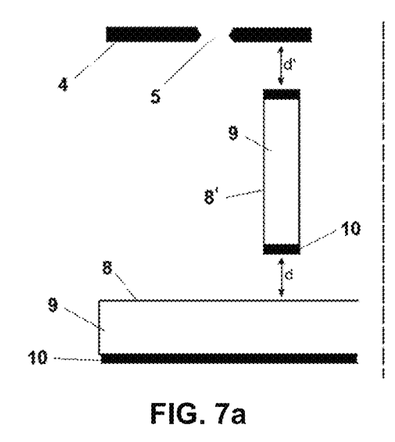
FIG. 7a-7b schematically describe a variation of the preceding figure. In this case, the active partitions have photodetectors and readout electronics attached directly on two of their (upper and lower) faces. Furthermore, said active partitions are separated from the main (horizontal) detector. The active partitions can also be inclined a certain angle with respect to the upper collimation element or with respect to the main detector.
Figure 7B:
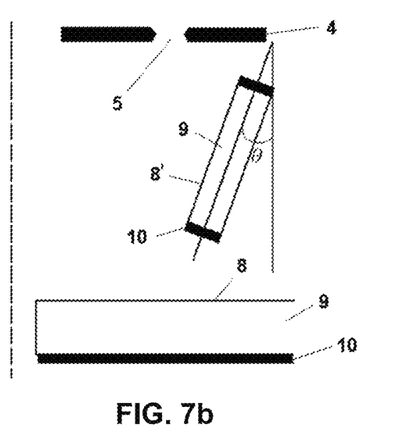

In another preferred embodiment of the invention, the separating partition and/or the detection assemblies (8, 8') are arranged in a perpendicular or oblique manner with respect to the plane defined by the collimation element (4), wherein said partition can furthermore be positioned at different distances (d, d') and at arbitrary angles (θ) with respect to the mentioned element (4). This situation is schematically illustrated in FIGS. 7a-7b herein.

Figure 9:
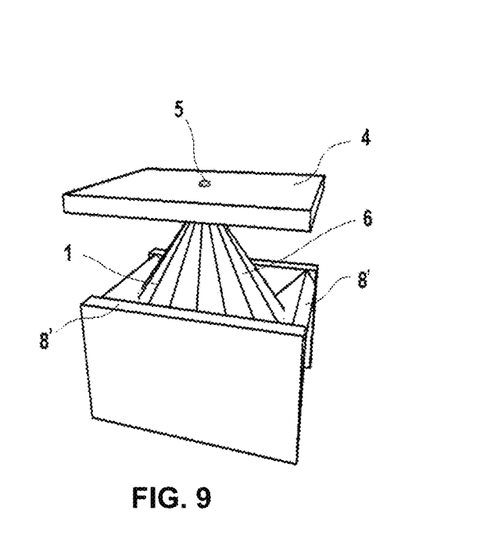
FIG. 9 shows a possible second version of the device of the invention, made up of four active partitions and a pinhole collimator, wherein the active partitions are oriented at an angle. Like in the case of FIG. 8, the main detector in this configuration is not necessary, and the active partitions must have photodetectors and attached readout electronics. The cone of incidence in the figure schematically shows the area wherein the rays can penetrate in the detection space of the device, due to the geometry and configuration of the pinhole collimator.

In another preferred embodiment of the invention, illustrated by FIGS. 8-9, at least one of the detection cells (3) comprises at least two detection assemblies (8, 8') arranged with their planes forming an angle with one another, such that the space subtended by said detection assemblies (8, 8') encompasses the entire cone (6) of incidence of the gamma rays (1).

In different preferred embodiments of the invention, the gamma ray absorption surfaces of the collimators having one or more openings (5) comprise dense materials having suitable thickness such that they are capable of stopping said gamma rays in the energy range of interest, such as Pb or W. Likewise, the geometry and the configuration of the aperture of each opening (5) can have any shape, inclination and radius.

The sensitive material (9) of the device for detection can be any material producing a measurable physical magnitude when the radiation interacts with said material. Some examples are scintillating, monolithic or pixelated crystals, semiconductors such as Si, Ge, CdTe, GaAs, Pbl2, Hgl2, CZT, etc. for solid-state detectors, xenon for scintillation and Cherenkov radiation detectors, etc. Furthermore, the sensitive materials (9) can be encapsulated or exposed, coupled to an optical reflective surface and/or using any known technique to improve the quality of the collected data. The optical reflective surfaces (13) can be polished or rough, specular, diffuse, retro-reflective or a combination thereof. Likewise, one or more detection assemblies (8, 8)' can comprise an optically painted surface.

In a detection system according to the invention, each detector device can be adjacent to another one forming a given assembly, and said assembly can be organized with respect to the other one, for example forming a closed or open structure. The components of a detector system can be identical or different, depending on their specific design conditions.

A detection assembly (8, 8') of the device can have an arbitrary shape, and can measure any physical magnitude which provides spatial and/or temporal information of at least one interaction cloud of one or more sensitive materials. Examples of such detection elements are solid-state detectors, scintillation detectors, etc.

Examples of solid-state detectors are semiconductors such as Si, Ge, CdTe, GaAs, $PbI_2$, $HgI_2$, CZT or HgCdTe (also known as CTM), Cherenkov radiators such as $PbF_2$, $NaBi(WO_4)_2$, PbWO4, $MgF_2$, $C_6F_{14}$, $C_4F_{10}$ or silica aerogel. Scintillator elements, such as organic or inorganic crystal scintillators, liquid scintillators or gas scintillators can also be used. Scintillators can produce a detection signal which is due both to scintillation processes and to Cherenkov radiation processes.

Organic crystal scintillators can be, for example, anthracene, stilbene, naphthalene, liquid scintillators (for example, organic liquids such as p-terphenyl ($C_{18}H_{14}$), 2-(4-biphenylyl)-5-phenyl-1,3,4-oxadiazole PBD ($C_{20}H_{14}N_{20}$), butyl PBD ($C_{24}H_{22}N_{20}$), PPO($C_{15}H_{11}NO$), dissolved in solvents such as toluene, xylene, benzene, phenylcyclohexane, triethylbenzene or decalin), gas scintillators (such as nitrogen, helium, argon, krypton, xenon), inorganic crystal scintillators, or combinations of any of the foregoing.

The commonly known inorganic scintillation crystals can be, for example, cesium iodide (CsI), thallium doped cesium iodide (CsI(Tl)), bismuth germanate (BGO), thallium doped sodium iodide (NaI(Tl)), barium fluoride ($BaF_2$), europium doped calcium fluoride ($CaF_2$(Eu)), cadmium tungstate ($CdWO_4$), cerium doped lanthanum chloride (LaCb(Ce)), cerium doped lutetium-yttrium silicates (LuYSiOs(Ce) (YAG (Ce)), silver doped zinc sulfide (ZnS(Ag)) or cerium (III) doped yttrium-aluminum granite $Y_3Al_5O_{12}$ (Ce) or LYSO. Additional examples are CsF, KI(TI), $CaF_2$(Eu), $Gd_2SiO_5$[Ce] (GSO), LSO.

As mentioned above, the scintillators according to the present invention can be monolithic crystals or pixelated crystals, or any combination thereof. Preferably, the scintillator, however, will be a single-crystal (monolithic block), given that pixelated crystals introduce more dead areas into the gamma ray detector, therefore providing less sensitivity to the detector device compared with single-crystals.

The device for detection (of scintillating photons) can be formed, for example, by photosensors. The photosensors can be matrices of silicon photomultipliers (SiPM), single-photon avalanche diodes (SPAD), digital SiPMs, avalanche photodiodes, position-sensitive photomultipliers, photomultipliers, phototransistors, photodiodes, photo-ICs or combinations thereof. This means that a detector device can be coupled, for example, to a SiPM matrix and another detector device can be coupled to a matrix of phototransistors in a detection system according to the preceding definitions.

In other embodiments of the invention, it is also possible to use multiple photodetectors (10) to provide a single data matrix. If a detector element is not large enough to cover a desired surface, it is possible to arrange two or more detectors in a matrix and combine their readouts to obtain a larger data matrix. The data matrix can be expressed using any desired coordinate system (Cartesian, cylindrical, spherical, etc.).

Figure 10:
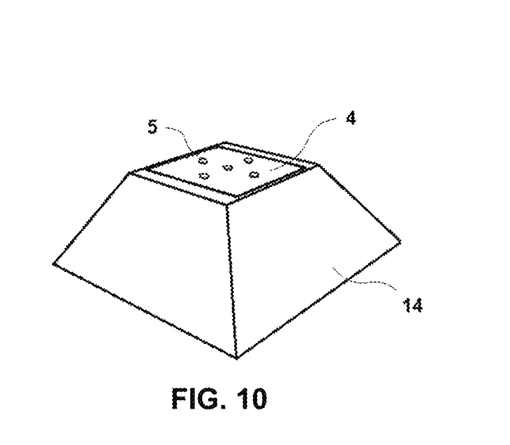
FIG. 10 shows a possible outer gamma ray shielding casing in a detection system according to the invention, which can be made up of Pb, W or the like, for the purpose of preventing the background noise coming from areas outside the field of view of interest.

Another object of the present invention relates to a system for generating images by means of the detection of gamma rays, comprising one or more devices according to any of the embodiments described herein. In said system, the electronic signal readout and processing means of the photodetectors (10) are preferably connected to a device for reconstructing images from the processing of said signals. An example of said system is schematically depicted in FIG. 10, wherein it can be seen how the system is configured with five collimation openings (5), associated with their respective collimation cells (3) (not shown in the figure), said cells being protected by a covering or casing (14) which preferably absorbs gamma radiation.

In a preferred embodiment of the system of the invention, the system can be arranged on a mobile platform adapted to be oriented towards different regions of the source (2) of gamma radiation.

The invention claimed is:

1. A device for the detection of gamma rays coming from a source, comprising at least two contiguous detection cells, wherein each of said detection cells comprises:
   a collimation element comprising an opening through which the gamma rays coming from the source can penetrate, defining a cone of incidence;
   a detection space adapted to receive the gamma rays that penetrate through the opening, wherein said detection space comprises one or more gamma ray detection assemblies; and wherein the theoretical projections of the cones of incidence of the gamma rays in two adjacent cells have an overlap volume within the detection space; the device being characterized in that at least one of the detection assemblies is arranged such that it stands in the way of the gamma rays coming into the overlap volume.

2. The device according to claim 1, wherein one or more detection assemblies comprise at least one gamma ray blocking surface.

3. The device according to claim 2, wherein the blocking surface is arranged as a separating partition between the detection cells, wherein said partition is in contact on both sides with detection assemblies of adjacent cells.

4. The device according to claim 3, wherein the separating partition and/or the detection assemblies are arranged in a perpendicular or oblique manner with respect to a plane defined by the collimation element.

5. The device according to claim 1, wherein at least one of the detection cells comprises at least two detection assemblies arranged with their planes forming an angle with one another, such that the space subtended by said detection assemblies encompasses the entire cone of incidence of the gamma rays.

6. The device according to claim 1, wherein one or more detection assemblies comprise one or more reflective elements for guiding the paths of the gamma rays.

7. The device according to claim 6, wherein at least one of the reflective elements comprises a rough or polished, retro-reflective or diffuse specular reflector or a combination thereof.

8. The device according to claim 1, wherein one or more detection assemblies comprise an optically painted surface.

9. The device according to claim 1, wherein at least one of the detection assemblies comprises a scintillating material as a gamma radiation-sensitive material and at least one photodetector connected to electronic signal readout and processing means of said photodetector.

10. The device according to claim 9, wherein the scintillating material comprises a pixelated solid, a monolithic solid, a liquid, gas or a combination thereof.

11. The device according to claim 9, wherein each detection cell comprises different scintillating materials.

12. The device according to claim 1, wherein the photodetector of at least one of the detection assemblies comprises photomultipliers, avalanche diodes, photodiodes, phototransistors, photo-ICs or a combination thereof.

13. The device according to claim 1, wherein at least one of the detection assemblies comprises a solid-state detector and/or a Cherenkov detector.

14. A system for generating images by means of the detection of gamma rays characterized in that it comprises one or more devices according to claim 1, with an electronic signal readout and processing means thereof being connected to a device for reconstructing images from the processing of said signals.

15. The system according to claim 14, wherein said system is arranged on a mobile platform adapted to be oriented towards different regions of the source of gamma radiation.

* * * * *